United States Patent
Hakkens et al.

(10) Patent No.: US 10,522,132 B2
(45) Date of Patent: Dec. 31, 2019

(54) DEFORMABLE ULTRASOUND ARRAY AND SYSTEM

(71) Applicant: KONINKLIJKE PHILIPS N.V., Eindhoven (NL)

(72) Inventors: Franciscus Johannes Gerardus Hakkens, Eindhoven (NL); Debbie Rem-Bronneberg, Eindhoven (NL); Wim Crooijmans, Eindhoven (NL); Cornelis Petrus Hendriks, Eindhoven (NL); Sergei Shulepov, Eindhoven (NL); Emil George Radulescu, Eindhoven (NL); Denny Mathew, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/572,286

(22) PCT Filed: Apr. 27, 2016

(86) PCT No.: PCT/EP2016/059369
§ 371 (c)(1),
(2) Date: Nov. 7, 2017

(87) PCT Pub. No.: WO2016/180636
PCT Pub. Date: Nov. 17, 2016

(65) Prior Publication Data
US 2018/0130457 A1 May 10, 2018

Related U.S. Application Data

(60) Provisional application No. 62/159,728, filed on May 11, 2015.

(30) Foreign Application Priority Data

Aug. 13, 2015 (EP) ..................... 15180855

(51) Int. Cl.
B06B 1/06 (2006.01)
G10K 11/35 (2006.01)
(Continued)

(52) U.S. Cl.
CPC .............. G10K 11/355 (2013.01); A61B 8/12 (2013.01); A61B 8/4227 (2013.01);
(Continued)

(58) Field of Classification Search
CPC ....... B06B 1/06; B06B 1/0603; B06B 1/0607; B06B 1/0688; B06N 1/0622
(Continued)

(56) References Cited

U.S. PATENT DOCUMENTS 7,063,666 B2  6/2006  Weng et al.
8,277,380 B2  10/2012  Daft et al.
(Continued)

FOREIGN PATENT DOCUMENTS

DE  102008028200 A1  12/2009
JP  02177944 A  7/1990

*Primary Examiner* — Derek J Rosenau

(57) ABSTRACT

Disclosed is an ultrasound array comprising a plurality of ultrasound transducer elements (20) on a carrier (10), said carrier further carrying an actuator arrangement (30, 30') of a material having an adjustable shape in response to an electromagnetic stimulus, e.g. an electro active polymer or optically responsive polymer, wherein the material is arranged to change the orientation of said ultrasound transducer elements in response to said stimulus. This facilitates configurable beam shaping and/or body contour matching with the ultrasound array. An ultrasound system (100) comprising such an ultrasound array is also disclosed.

12 Claims, 8 Drawing Sheets

(51) Int. Cl.

| | |
|---|---|
| *A61B 8/00* | (2006.01) |
| *A61B 8/12* | (2006.01) |
| *G10K 11/32* | (2006.01) |
| *G01N 29/06* | (2006.01) |
| *G01N 29/24* | (2006.01) |
| *G01N 29/26* | (2006.01) |
| *G01S 15/89* | (2006.01) |
| *G01S 7/00* | (2006.01) |
| *G01S 15/00* | (2006.01) |
| *A61N 7/02* | (2006.01) |

(52) U.S. Cl.
CPC .......... *A61B 8/4281* (2013.01); *A61B 8/4461* (2013.01); *A61B 8/4483* (2013.01); *A61B 8/4488* (2013.01); *A61B 8/4494* (2013.01); *A61B 8/54* (2013.01); *A61N 7/022* (2013.01); *B06B 1/06* (2013.01); *G01N 29/0654* (2013.01); *G01N 29/2456* (2013.01); *G01N 29/262* (2013.01); *G01S 7/00* (2013.01); *G01S 15/00* (2013.01); *G01S 15/8929* (2013.01); *G10K 11/32* (2013.01)

(58) Field of Classification Search
USPC ........................................ 310/322, 334, 335
See application file for complete search history.

(56) References Cited

U.S. PATENT DOCUMENTS

| | | | |
|---|---|---|---|
| 2003/0135135 A1* | 7/2003 | Miwa | A61N 7/00 601/2 |
| 2006/0224090 A1 | 10/2006 | Ostrovsky et al. | |
| 2008/0125661 A1 | 5/2008 | Garbini et al. | |
| 2009/0010459 A1 | 1/2009 | Garbini et al. | |
| 2011/0248603 A1* | 10/2011 | Tezuka | A61B 8/4405 310/314 |
| 2012/0209121 A1 | 8/2012 | Boudier | |
| 2012/0296214 A1 | 11/2012 | Urabe et al. | |
| 2014/0111480 A1 | 4/2014 | Kim et al. | |
| 2014/0180126 A1 | 6/2014 | Millett et al. | |

\* cited by examiner

DEFORMABLE ULTRASOUND ARRAY AND SYSTEM

This application is the U.S. National Phase application under 35 U.S.C. § 371 of International Application No. PCT/EP2016/059369, filed on Apr. 27, 2016, which claims the benefit of Provisional Application Ser. No. 62/159,728, filed May 11, 2015 and EP Application 15180855.7 filed Aug. 13, 2015. These applications are hereby incorporated by reference herein.

FIELD OF THE INVENTION

The present invention relates to a deformable ultrasound array comprising a plurality of ultrasound transducer elements.

The present invention further relates to an ultrasound system comprising such a deformable ultrasound array.

BACKGROUND OF THE INVENTION

Ultrasound waves find several applications in medicine. One such application is ultrasound imaging, wherein ultrasound waves are emitted by an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by ultrasound transducer elements and are focused on diseased tissue. The significant energy deposition at the focus creates local temperatures in the range of about 65° C. to 85° C., which destroys the deceased tissue by coagulative necrosis.

Such applications face several challenges. For instance, in imaging applications it is far from trivial to achieve a good contact between the ultrasound transducer array and the part of the body to be imaged. This is typically achieved by using special gels that improve the contact between the ultrasound transducer array and the body part. However, a drawback of this approach is that usually large amounts of gel have to be used, which may contain air bubbles that interfere with the transmission or reception of the ultrasound signals. Moreover, the ultrasound transducer array, e.g. in the form of the probe, is typically hand-held during an imaging procedure, which makes the procedure prone to errors.

Similar challenges exist in therapeutic applications, where the focused beam requires periodic readjustment to treat multiple regions of the diseased tissue. This may be done manually by adjusting a focusing element or by beam steering by adjustment of the relative phases of the signals generated by the respective ultrasound transducer elements. The manual adjustment is prone to inaccuracies and the range of phase controlled beam steering may not be sufficient to reach all diseased tissue without array displacement. A further complication is that therapeutic treatments such as HIFU treatments is often monitored by magnetic resonance imaging, such that the materials in the ultrasound transducer array must be compatible with magnetic resonance techniques, e.g. must be diamagnetic.

US 2008/0125661 A1 discloses an ultrasound transducer array including a shape memory alloy. This allows the array to be switched between two geometries, namely an actual geometry and a geometry 'remembered' by the shape memory allow. The memory of the alloy may cause a desired change in array geometry during manufacture, such as a shape memory alloy twisting an array into a curved or helix due to applied heat. The array may be fixed in place by the memory alloy or bonding after positioning by the memory alloy, preventing further substantial alteration. It is a drawback that such an array is difficult to control and must be controlled by heat, which is problematic.

SUMMARY OF THE INVENTION

The present invention seeks to provide an ultrasound array having a more versatile adjustable shape for adjusting to a body part to be imaged or treated and/or for adjusting the beam direction produced by the array.

The present invention further seeks to provide an ultrasound system including such an ultrasound array.

According to an aspect, there is provided an ultrasound array comprising a plurality of ultrasound transducer elements on a carrier further carrying an actuator arrangement of a material having an adjustable shape in response to an electromagnetic stimulus, wherein the material is arranged to change the orientation of said ultrasound transducer elements in response to said stimulus.

The invention is based on the realization that the availability of a new class of materials that are capable of shape changes in response to an electromagnetic stimulus such as a voltage, current or light facilitates a configurable change in the orientation of an ultrasound array including such a material actuator arrangement. Examples of such materials are electro active polymers and optically responsive polymers. This for instance makes it possible to conform the shape of the ultrasound array to a body contour to be imaged or treated, thereby obviating the need for the use of large amounts of gel to achieve a satisfactory contact between the array and the body portion and/or the need to manually hold the array in place. It for instance also makes it possible to adjust the beam direction produced by the ultrasound array by adjusting the orientation of individual ultrasound transducer elements and/or groups of ultrasound transducer elements.

In an embodiment, the actuator arrangement comprises a plurality of material portions, wherein each portion is located between the carrier and a peripheral portion of one of said ultrasound transducer elements. Each portion may be individually addressable, i.e. individually provided with the electromagnetic stimulus such that the orientation of transmission surface of individual ultrasound transducer elements may be altered in response to the application of such a stimulus, for instance for the purpose of beam shaping.

In an alternative embodiment, the actuator arrangement is arranged to simultaneously change the orientation of a further plurality of said ultrasound transducer elements in response to said stimulus, wherein the further plurality is at least a subset of the plurality. In this embodiment, a group of ultrasound transducer elements may be mounted on a single portion of the material such that actuation of this portion adjusts the orientation of the group in a correlated manner.

The actuator arrangement may comprise a foil extending over said carrier such that upon deformation of the foil the orientation of the ultrasound transducer elements mounted on said foil is adjusted in accordance with this deformation. This for instance is particularly suitable to deform the array in a single direction.

The actuator arrangement may comprise a plurality of strips extending over said carrier. The strips may be individually addressable to increase the control over the deformation of the array.

The actuator arrangement may further comprise a further plurality of strips extending over said carrier, said further plurality of strips running in a perpendicular direction to the plurality of strips to form a mat actuator arrangement. This facilitates the deformation of the array in multiple directions. The further plurality of strips may be individually addressable to further increase the control over the deformation of the array.

The plurality of strips and the further plurality of strips may form an interwoven mat actuator arrangement to facilitate the deformation of the array in multiple directions.

The ultrasound transducer elements may be aligned with respective junctions of said mat actuator arrangement or with respective vacancies in said mat actuator arrangement that are delimited by neighboring pairs of strips from the plurality of strips and neighboring pairs of strips from the further plurality of strips.

In an embodiment, the actuator arrangement comprises an array of annular material portions distributed over said carrier. The annular material portions may be individually addressable. Such annular portions also facilitate the deformation of the array in multiple directions.

The carrier may be flexible and may be located in between the plurality of ultrasound transducer elements and the actuator arrangement. This for instance facilitates the provision of the connections to the ultrasound transducer elements through the flexible carrier, e.g. a flexible PCB.

The ultrasound array may further comprise a protective foil, wherein the actuator arrangement is located in between the carrier and the protective foil. This protects the material actuator arrangement from damage by external influences.

In an embodiment, the ultrasound array further comprises a strap to which the array is attached for securing the array against a body part. This further secures the array against the body part, thus further reducing the risk of imaging or treatment artefacts due to the unintentional displacement of the array during a procedure.

According to another aspect, there is provided an ultrasound system comprising the ultrasound array of any of the aforementioned embodiments, an ultrasound signal generating stage coupled to the ultrasound transducer elements; and an electromagnetic stimulus generator coupled to the actuator arrangement of the material having an adjustable shape. Such an ultrasound system for instance may be used for ultrasound treatments, in which a focused ultrasound beam is delivered to diseased tissue as previously explained.

The ultrasound system may further comprise an ultrasound imaging processing stage coupled to the ultrasound transducer elements for generating an ultrasound image from ultrasound echoes received by at least some of the ultrasound transducer elements. Such an ultrasound system for instance may be used for ultrasound imaging, in which ultrasound echoes are collected and processed by the ultrasound imaging processing stage to generate the ultrasound image.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
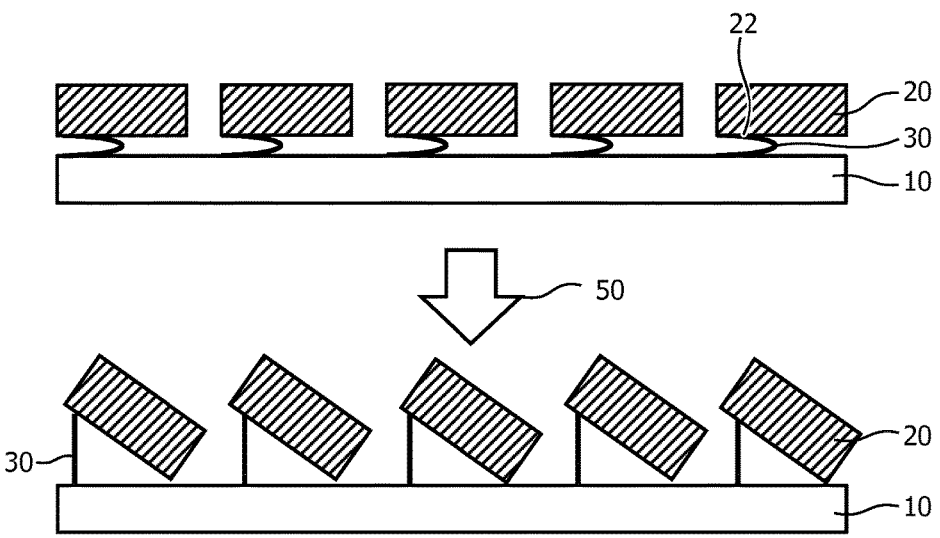
FIG. 1 schematically depicts a cross-sectional view of an ultrasound array according to an embodiment.

It should be understood that the Figures are merely schematic and are not drawn to scale. It should also be understood that the same reference numerals are used throughout the Figures to indicate the same or similar parts.

Embodiments of the present invention relate to an ultrasound array in which the orientation of the ultrasound transducer elements relative to a normal plane can be adjusted by an actuator arrangement of a material having an adjustable shape in response to an electromagnetic stimulus, wherein the material is arranged to change the orientation of said ultrasound transducer elements in response to said stimulus. In the context of the present application, such a material is characterized by showing a correlation between the degree of deformation and a range of strengths of the electromagnetic stimulus such that the degree of deformation of the material may be (reversibly) controlled by the strength of the applied electromagnetic stimulus. This therefore excludes shape memory materials, as the degree of deformation of such materials cannot be accurately controlled; instead such materials typically are driven between two shapes only, i.e. an 'on'-shape after application of such stimulus, typically heat, and an off-shape prior to the application of such a stimulus.

In the context of the present application, an electromagnetic stimulus includes electric stimuli such as an electric field, such as a voltage difference, or an electric current, as well as optical stimuli, i.e. electromagnetic radiation, of a suitable wavelength or spectral composition.

In the context of the present application, where reference is made to ultrasound transducer elements, it should be understood that any suitable type of ultrasound transducer element may be contemplated, such as a piezoelectric transducer element, e.g. a lead zirconate titanate (PZT) ultrasound transducer element or a capacitive micro machined ultrasound transducer (CMUT) element. CMUT transducer elements are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices can have dimensions in the micrometer to millimeter range, e.g. up to several millimeters, with spacing between the individual diaphragms less than a few micrometers. Many such individual CMUT elements can be connected together and operated in unison as a single transducer element. For example, four to sixteen CMUTs can be coupled together to function in unison as a single transducer element. A typical 2D transducer array can have several thousand CMUT transducer elements, e.g. up to 10,000 CMUT elements, which facilitates the constructions or transducer arrays having dimensions of several decimeters. The ultrasound transducer elements or tiles may have any suitable shape, e.g. square, rectangular, circular and may have any suitable dimension. As the provision of such ultrasound transducer elements is well-known per se, this will not be explained in further detail for the sake of brevity only. In an embodiment, individual ultrasound elements may be organized in groups of pixels that are operated as a group. The ultrasound array may comprise a plurality of such groups. In the remainder, where reference is made to ultrasound transducer elements, this may refer to the smallest controllable unit of an ultrasound array, e.g. a single pixel or a group of pixels operated at the group level.

FIG. 1 schematically depicts an ultrasound array comprising a plurality of ultrasound transducer elements 20 on a carrier 10. The carrier 10 may be any suitable carrier, e.g. a rigid carrier such as a semiconductor, e.g. silicon or glass carrier, or a flexible carrier, e.g. a polymer carrier. The carrier 10 carries an actuator arrangement 30 comprising a plurality of actuators, wherein each actuator is made of a material having an adjustable shape in response to an electromagnetic stimulus 50, wherein the material is arranged to change the orientation of the ultrasound transducer elements 20 in response to said stimulus. Although not specifically shown, each actuator typically comprises a suitable electrode arrangement for actuating the actuator, which will be explained in more detail below. The electrode arrangement may be arranged such that all actuators are actuated by a single electromagnetic stimulus or may be arranged such that multiple electromagnetic stimuli may be provided simultaneously to the arrangement 30, with different stimuli addressing different subsets of actuators. In an embodiment, each actuator of the actuator arrangement 30 is individually addressable. Here the actuator arrangement 30 comprises a plurality of material portions, wherein each portion is located between the carrier 10 and a peripheral portion 22 of one of the ultrasound transducer elements 20. Each portion may be individually addressable, i.e. individually provided with the electromagnetic stimulus such that the orientation of transmission surface of individual ultrasound transducer elements may be altered in response to the application of such a stimulus, for instance for the purpose of beam shaping.

Although not specifically shown, the ultrasound transducer elements 20 typically comprise electrically conductive connections for providing the ultrasound transducer elements 20 with drive signals and optionally for receiving echo signals from the ultrasound transducer elements 20. Such connections may be made of any suitable electrically conductive material. In an embodiment, the connections are comprised in the carrier 10. Alternatively, the ultrasound transducer elements 20 may be interconnected, e.g. form a ribbon or a grid, by flexible polymer portions, e.g. polyimide portions, which carry or embed the connections. This is known per se and is sometimes referred to as flex-to-rigid technology.

Each actuator of the actuator arrangement 30 is typically connected between an off-center portion of an ultrasound transducer element 20, e.g. a peripheral region of the ultrasound transducer element 20 and the carrier 10 such that upon application of the electromagnetic stimulus, or electromagnetic stimuli, the actuators of the actuator arrangement 30 deform in accordance with the strength of the applied stimulus and the off-center portion of the ultrasound transducer element 20 is displaced relative to the carrier 10 by the deformation of its associated actuator, as shown in the bottom part of FIG. 1. This changes the angle under which the ultrasound transducer element 20 generates its ultrasound transmission and can therefore be used to steer the beam generated by the ultrasound array ultrasound transducer elements 20. Alternatively, the actuator arrangement 30 may be arranged to deform both the carrier 10 and the matrix or array of ultrasound transducer elements 20. It will be readily understood that the beam may be steered over a range of angles by altering the strength of the applied electromagnetic stimulus, e.g. the strength of the electric field or the intensity of the electromagnetic radiation applied across each actuator. Moreover, it will be readily understood that by having individually addressable actuators within the actuator arrangement 30, the beam shape can be controlled in a fine-grained manner, thus not only facilitating the adjustment of the beam angle, but also facilitating the adjustment of the beam profile generated by the ultrasound array.

Although not specifically shown in FIG. 1 or in the following embodiments of the ultrasound array, the ultrasound transducer elements 20 may be covered by a coupling material for coupling the elements to tissue or blood in case of the ultrasound transducer elements 20 being integrated in a catheter or the like. Suitable embodiments of such a coupling material include a foil over the ultrasound transducer element matrix, an acoustic window material on each ultrasound transducer element 20, and so on. If in an enclosure such as a catheter tip, the coupling material may be a gel, fluid and so on. Alternatively in such an enclosure the coupling material may form (part of) the wall of the enclosure to which the ultrasound transducer elements 20 are directly coupled.

Figure 2:
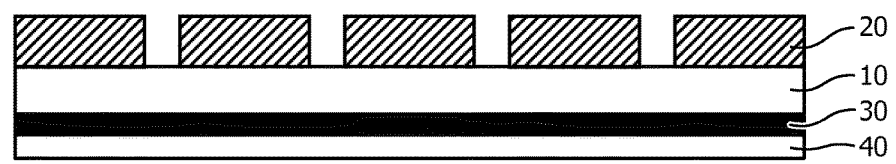
FIG. 2 schematically depicts a cross-sectional view of an ultrasound array according to another embodiment.

FIG. 2 schematically depicts a further embodiment of an ultrasound array. In this embodiment, the actuator arrangement 30 of the material having an adjustable shape, i.e. a deformable material, in response to an electromagnetic stimulus 50 is provided in the form of a foil or film of the material, wherein the carrier 10, here a flexible carrier, is located in between the actuator arrangement 30 and the ultrasound transducer elements 20. A protective foil 40 may be provided over the actuator arrangement 30 to protect the actuator arrangement 30 from damage, e.g. to protect the electrode arrangement (not shown) on the actuator arrangement 30. In this embodiment, the flexible carrier 10 may be provided in the form of a backing foil containing the aforementioned connections of the ultrasound transducer elements 20. Alternatively or additionally, the protective foil 40 may cover the ultrasound array 20. The protective foil 40 may be an elastic foil, e.g. a foil comprising a (thermoplastic) elastomer such as silicone rubber, rubber, a thermoplastic elastomer or a soft thermoplastic such as polyurethane or a polyether block amide. If the protective foil 40 covers the ultrasound transducer array, the foil material preferably is acoustically impedance matched to the array. For a thin protective foil 40 or a foil placed on the neutral axis of the actuator arrangement, a stiffer material such as polyamide or polyimide may also be used. Other suitable materials for the protective foil 40 will be immediately apparent to the skilled person.

Upon actuation of the foil by the provision of the electromagnetic stimulus 50, the ultrasound array may deform as shown in the bottom part of FIG. 2, typically by an in-plane expansion leading to a reduction in thickness of the actuator arrangement 30. This for instance may be used to adjust the beam shape produced by the ultrasound transducer elements 20 of the ultrasound array and/or to conform the ultrasound array to a surface on which the array is placed, e.g. a part of the body of a patient, wherein the actuated ultrasound array is deformed to match the contours of the body portion. This for instance ensures a good contact between the ultrasound array and the body portion, thereby obviating the need for (large amounts of) contact gel between the ultrasound array and the body portion to achieve the desired close contact. This for instance may be beneficial during transthoracic echo generation, where the deformation of the ultrasound array can be used to push the array into the intercostal space to obtain a good quality image of the heart. Alternatively, the ultrasound array may be placed and controlled such as to steer the generated ultrasound beam in between the ribs. Moreover, by wrapping the array around the region of interest, ultrasound transducer elements 20 may be positioned more or less perpendicular to this region, thus obviating the need for excessive electronic beam steering. This therefore improves the image quality of an ultrasound image generated with such an ultrasound array.

Figure 3:
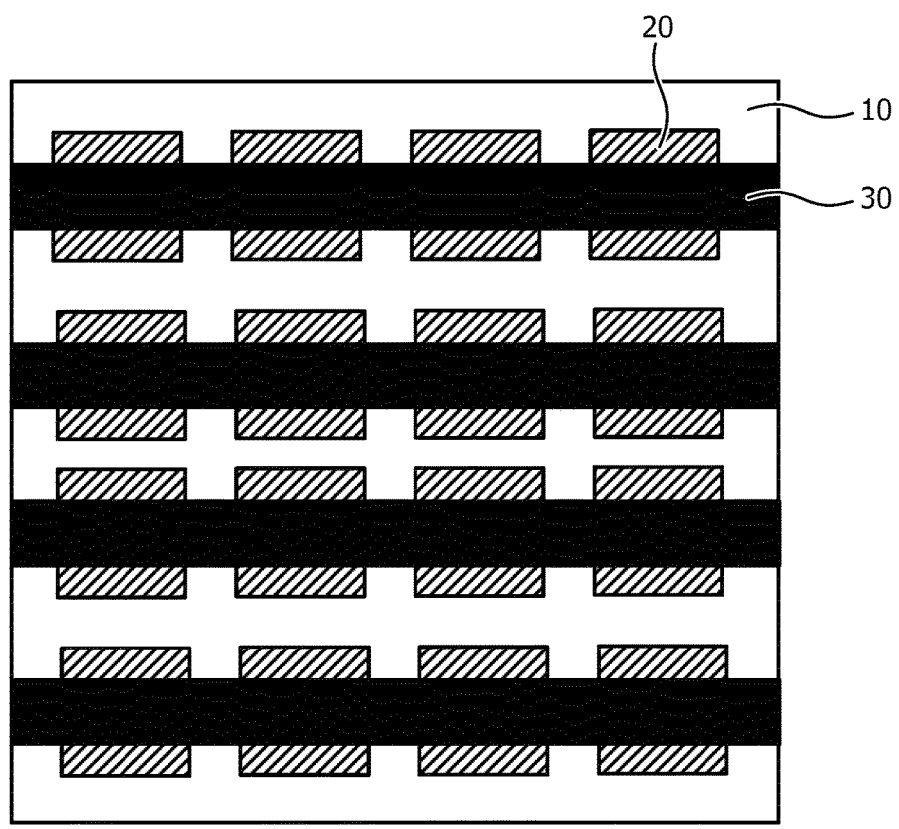
FIG. 3 schematically depicts a through view of an ultrasound array according to yet another embodiment.

In order to obtain a more fine-grained control over the beam steering and/or body contour matching of the ultrasound array, the foil-based actuator arrangement 30 may be replaced with an actuator arrangement 30 as shown in FIG. 3, wherein the arrangement comprises a plurality of individually addressable actuator strips, here organized in rows by way of non-limiting example. As before, the flexible carrier 10 may be located in between the actuator arrangement 30 and the ultrasound transducer elements 20. The ultrasound transducer elements 20 may be grouped in rows, wherein each row aligns with an actuator strip to ensure that a deformation of such a strip equates to a corresponding deformation in the orientation of the ultrasound transducer elements 20 associated with the actuator strip.

Figure 4:
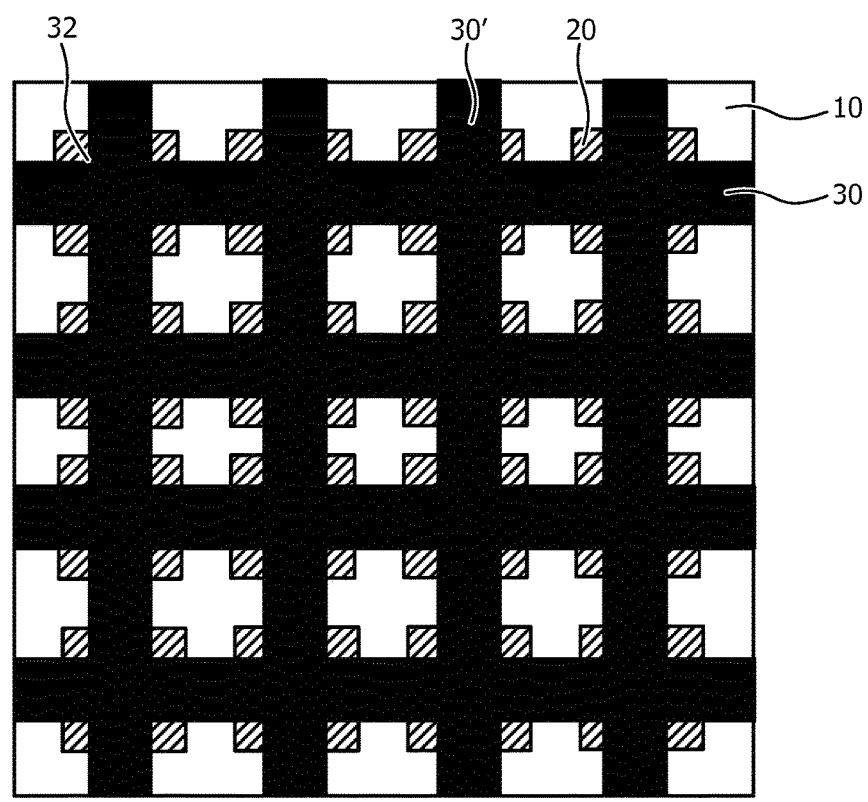
FIG. 4 schematically depicts a through view of an ultrasound array according to yet another embodiment.

The embodiment in FIG. 3 facilitates an out-of-plane deformation of the ultrasound array in a major direction as governed by the orientation of the actuator strips of the actuator arrangement 30, e.g. to facilitate 1D beam forming. In order to facilitate an out-of-plane deformation in multiple directions, e.g. to facilitate 2D beam forming or to facilitate more intimate contact with a body portion, the actuator arrangement 30 may further comprise a plurality of individually addressable further actuator strips 30' as schematically shown in FIG. 4. The further actuator strips 30' and the actuator strips 30 define an actuator arrangement in the form of a mat, i.e. a mat actuator arrangement, wherein at least some of the actuator strips 30 may overlay the further actuator strips 30', wherein at least some of the further actuator strips 30' may overlay the actuator strips 30 and/or wherein at least some of the actuator strips 30 are woven through the further actuator strips 30'. In an embodiment, all actuator strips 30 are woven through the further actuator strips 30' to form an interwoven mat actuator arrangement.

Figure 5:
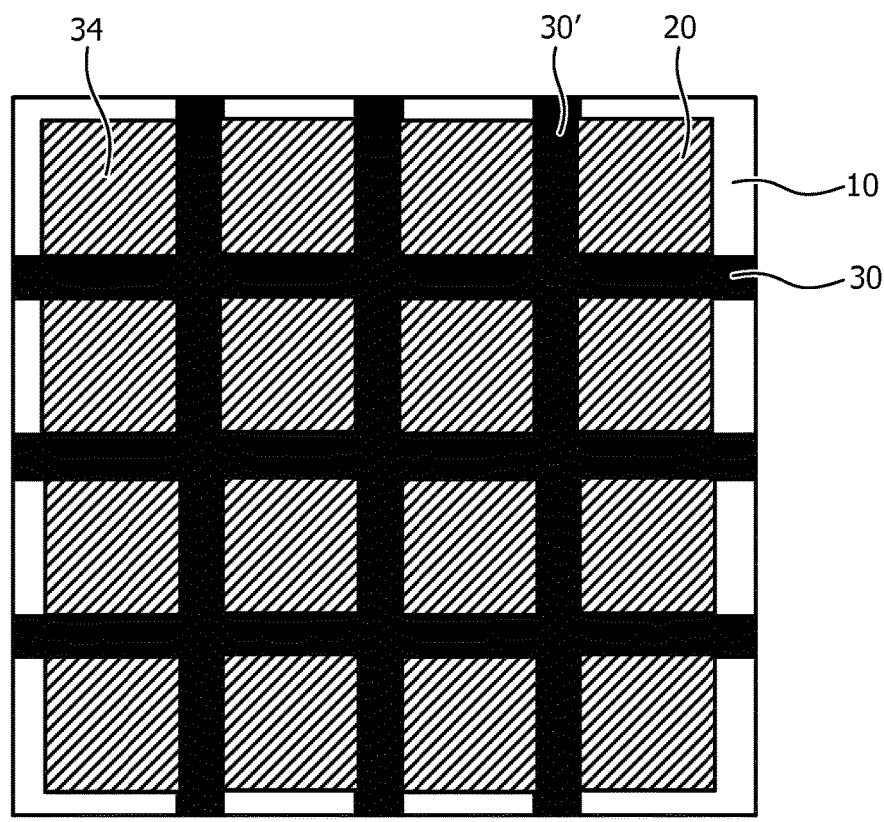
FIG. 5 schematically depicts a through view of an ultrasound array according to yet another embodiment.

In FIG. 4, the ultrasound transducer elements 20 are placed over the junctions 32 between an actuator strip 30 and a further actuator strip 30'. In this embodiment a surface portion of the ultrasound transducer elements 20 may be bonded to the junctions 32 to facilitate displacement of the ultrasound transducer elements 20 upon actuation of the actuator arrangement. FIG. 5 schematically depicts an alternative embodiment, in which the ultrasound transducer elements 20 are placed over the vacancies or voids 34 in the mat actuator arrangement, wherein each void is delimited by a pair of neighboring actuator strips 30 and a pair of neighboring further actuator strips 30'. In this embodiment the entire surface of the ultrasound transducer elements 20 may be bonded to the contact surface including the actuator arrangement, e.g. along edge portions of the ultrasound transducer elements 20, to facilitate displacement of the ultrasound transducer elements 20 upon actuation of the actuator arrangement. In an embodiment, some lateral spacing may exist between the actuator strips 30 and the further actuator strips 30' on the one hand and the ultrasound transducer elements 20, wherein the ultrasound transducer elements 20 are redirected by deformation of the carrier 10 induced by selective actuations of the actuator strips 30 and/or the further actuator strips 30'.

Such a mat actuator arrangement allows for precise beam profile forming and/or body contour matching by selective deformation of the actuator strips 30 and further actuator strips 30' in terms of which strips are deformed as well as in terms of to what extent the selected strips are deformed by application of an electromagnetic stimulus having a strength tailored to the desired degree of deformation of the strip or further strip the stimulus is applied to.

At this point it is noted that although in a preferred embodiment each of the actuator strips 30 and further actuator strips 30' are individually addressable, it is equally feasible that at least some of the actuator strips 30 and further actuator strips 30' are grouped together and addressed at the group level by an appropriate electromagnetic stimulus. Moreover, each of the actuator strips 30 and further actuator strips 30' may include individually addressable actuator elements (not shown).

Figure 6:
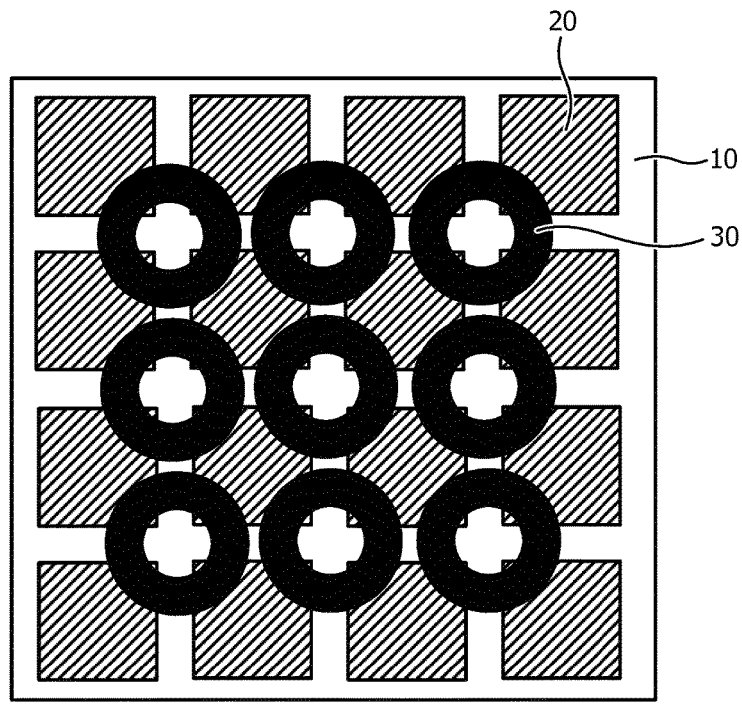
FIG. 6 schematically depicts a through view of an ultrasound array according to yet another embodiment.

It is furthermore noted that it is not necessary for the actuator arrangement to be shaped as a mat arrangement to facilitate out-of-plane deformation of the ultrasound array in multiple directions. Any suitable actuator arrangement may be provided for this purpose. A suitable alternative embodiment is schematically depicted in FIG. 6 by way of non-limiting example, in which the mat actuator arrangement is replaced by a plurality of preferably individually addressable annular actuators 30 laid out in a grid on the flexible substrate 10 in between the actuators and the ultrasound transducer elements 20. By actuating selected annular actuators 30, the ultrasound array may be deformed in multiple directions as will be readily understood by the skilled person. Other variations will be apparent to the skilled person, such as an actuator arrangement in which each actuator element can bend in two directions, which for instance may be achieved by using aligned polymer materials, by using different materials for each actuator, and/or by using a plurality of electrode arrangements for each actuator, wherein different electrode arrangement invoke a deformation of the actuator in a different direction.

Figure 7:
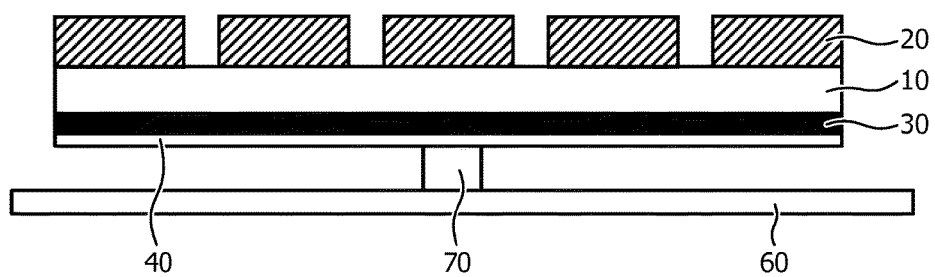
FIG. 7 schematically depicts a cross-sectional view of an ultrasound array according to yet another embodiment.

The ultrasound array according to embodiments may be shaped as a standalone flexible array or as a flexible part of a holding apparatus, e.g. an external probe or catheter, in which case the ultrasound array may be located in the catheter tip and/or as part of an in-body system, e.g. for endovascular, interstitial or natural orifice investigations. The ultrasound array may further comprise securing means such as a strap 60 for securing the ultrasound array against a part of the body of a patient, as is schematically depicted in FIG. 7. The strap 60 may be made of any suitable material, e.g. leather, plastic or textile and may use any suitable locking mechanism, e.g. a clasp, buckle or Velcro to secure the ultrasound array against the body part. A contact button 70 securing the strap 60 to the ultrasound array may also be present. The contact button 70 may connect the bendable ultrasound array to the strap 60. In this way, the array can bend without having to deform the strap 60. If the array would be connected over the complete surface to the strap 60, the strap would also need to deform when the actuator arrangement is actuated, which would require excessive force.

In the foregoing embodiments, where the ultrasound array is used for generating ultrasound images, it may be decided by visual inspection which actuators of the actuator arrangement 30 need to be actuated in order to obtain the desired image. Alternatively, an automated procedure using optimization algorithms may be employed to determine which actuators require actuation. In some embodiment, a thin layer of coupling gel may still be used to further enhance the contact between the ultrasound array and a body region. In the foregoing embodiments, the electrode arrangement for the actuator arrangement may comprise electrodes on opposite faces of the deformable material, e.g. an electro active polymer (EAP) layer. These provide a transverse electric field for controlling the thickness of the EAP layer. This in turn causes expansion or contraction of the EAP layer in the plane of the layer.

The electrode arrangement for the actuator arrangement may instead comprise a pair of suitably shaped electrodes such as comb electrodes on one face of the actuator material, e.g. on each actuator portion. This provides in-plane electric field, for directly controlling the dimensions of the layer in-plane.

In each of the foregoing embodiments, the electrode arrangement may be arranged such that all actuators are actuated by a single electromagnetic stimulus or may be arranged such that multiple electromagnetic stimuli may be provided simultaneously to the arrangement 30, with different stimuli addressing different subsets (groups) of actuators. In an embodiment, each actuator of the actuator arrangement 30 is individually addressable.

Materials that may be deformed in response to an electromagnetic stimulus are known per se, and any suitable material may be used for this purpose. The material for instance may be an electro-active polymer. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers include, but is not limited to acrylates, polyurethanes, silicones.

The sub-class conjugated polymers include, but are not limited to:

polypyrrole, poly-3,4-ethylenedioxythiophene, poly(p-phenylene sulfide), polyanilines.

Alternatively, the actuator material may be a material that is deformable by the provision of an electromagnetic stimulus in the form of electromagnetic radiation, e.g. visible or UV light. Such materials are also known per se. For example, the actuator material may include an optically responsive polymer, e.g. polymers based on azo compounds.

The actuator material may contain a mixture of reactive liquid crystals and reactive azo compounds that are liquid crystalline or at least align with the liquid crystals and that are polymerized in the liquid crystalline state to obtain films with aligned molecules. Such alignment may be achieved over large areas to obtain so-called mono-domain materials. Alignment over smaller areas leads to obtaining so-called multi-domain materials.

Alternatively, other isomerizable double bond-containing polymers such as polyimides and polyesters that are not liquid crystalline but give rise to similar effect when irradiated may be used. These materials are less preferred as they have high glass temperatures, which increase their response times. The response of the liquid crystal-based responsive materials is driven by the fact that upon cis-trans isomerization of the double bond of the polymer the order in the polymerized material is decreased leading to a contraction of the material in the direction of the alignment and an expansion in the other two directions, as is known per se.

Any suitable optical stimulus may be applied to such optically responsive materials, e.g. a lamp, laser or the like. In an embodiment, the optical stimulus may be provided through an optical element such as a fibre, light guide including out-coupling features, e.g. surface textures, portions with particular refractive indices to induce out-coupling, and so on.

Additional passive layers may be provided for influencing the behavior of the EAP layer in response to an applied electric field.

The actuator arrangement may be sandwiched between respective electrodes or may be provided with respective electrodes on one side of the actuator material as previously explained. The electrodes may be stretchable so that they follow the deformation of the actuator material. Materials suitable for such electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS) or composite materials such as elastomers filled with conductive particles. Metalized polyester films may also be used, such as metalized polyethylene terephthalate (PET), for example using an aluminum coating.

The materials for the different layers may be selected for example taking account of the elastic moduli (Young's moduli) of the different layers.

Additional layers to those discussed above may be used to adapt the electrical or mechanical behavior of the device, such as additional polymer layers.

In order to demonstrate the proof of concept, a bio-heat model has been constructed for a transurethral prostate application using a HIFU ultrasound system. In this simulation, a row of four CMUT elements each having a transducer area of 4×5 mm with neighboring CMUT elements being spaced apart by 1 mm was simulated on a planar carrier and on a deformed carrier having an out-of-plane deformation of about 1 mm at the edges of the carrier. Each CMUT element was driven at 15 W/cm$^2$ into a simulated tissue having an attenuation of 0.4 dB/cm/MHz at a temperature of 37° C., with the outer walls of the prostate at 40 mm from the entry surface of the tissue.

Figure 8:
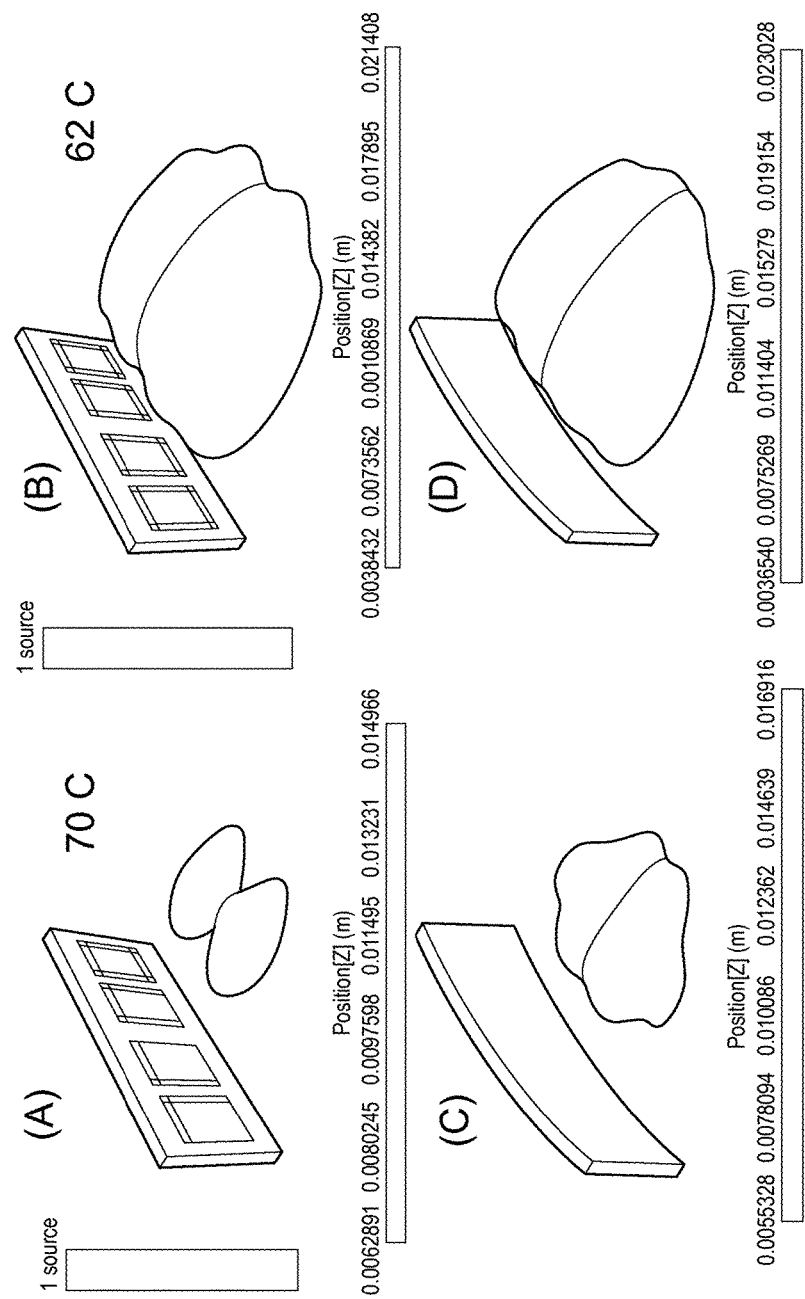
FIG. 8 A)-D) depicts a visualization of a bio heat model simulation of the effect on heat generation in tissue resulting from different ultrasound array geometries.

FIG. 8 depicts the iso-zones (an area of temperature boundary) at 70° C. (A and C) and 62° C. (B and D) respectively, for a planar carrier (A and B) and curved carrier (C and D) respectively. In particular the iso-zone at 70° C.

is strongly affected (increased) by the curvature, thus demonstrating that such curvature can be used to heat larger tissue areas, e.g. for such a prostate treatment application. Although less dramatically, the shape of the iso-zone at 62° C. has also altered, thus indicating that curvature control can be used for increased therapy control; as a result of acoustic beam forming, the ultrasound energy can be more focused within the tissue such that more energy is deposited at a certain location. Consequently, the region of interest can reach a temperature threshold more quickly.

The simulations were performed with STAR-CCM+ from CD-Adapco. The model includes a Pennes-like formulation (for bioheat transfer), i.e., thermal source is due to absorption of the propagating ultrasound waves, thermal "leak" is due to blood perfusion (taken uniform over the tissue), and soft tissue is described by its thermodynamic properties (such as density, thermal conductivity, heat capacity). The acoustic properties were kept constant in time with acoustic impedance in the range of 1.5-1.65 MRayls and absorption in the range 0 (lossless media)-0.5 dB/cm/MHz. The thermal model is based on a generalized bioheat equation, wherein the tissue's heat conductivity was taken 0.4-0.5 W/mK and heat capacity 2500-3500 J/kg/K. The blood perfusion term was included on basis of an effective heat source (leak), corresponding to the perfusion rate between 0-0.5 mL/g/min.

Figure 9:
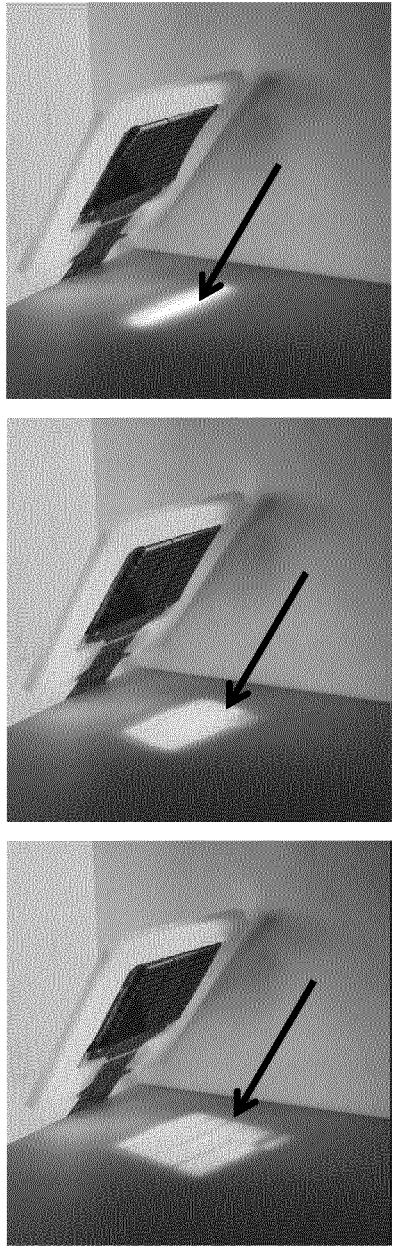
FIG. 9 shows a series of photographs of a light spot reflected by an ultrasound array according to an embodiment in different geometries.

To further demonstrate proof of concept for the beam shaping, an array of CMUT elements on a foil of an electro active polymer was provided, with an electrode arrangement (finger electrodes) on one side of the foil to facilitate out-of-plane bending of the foil. A light beam was directed under a non-perpendicular angle onto the CMUT array such that the light reflected by the CMUT array was projected onto a wall. FIG. 9 shows a series of images wherein the foil was progressively curved going from left to right by the application of an increasing electric field across the foil. As indicated by the arrows, the reflection of the light beam as projected onto the wall by the CMUT array is progressively changing shape, thus demonstrating that the shape of the CMUT array can be altered to control the (1D) beam shape generated by the CMUT array.

Figure 10:
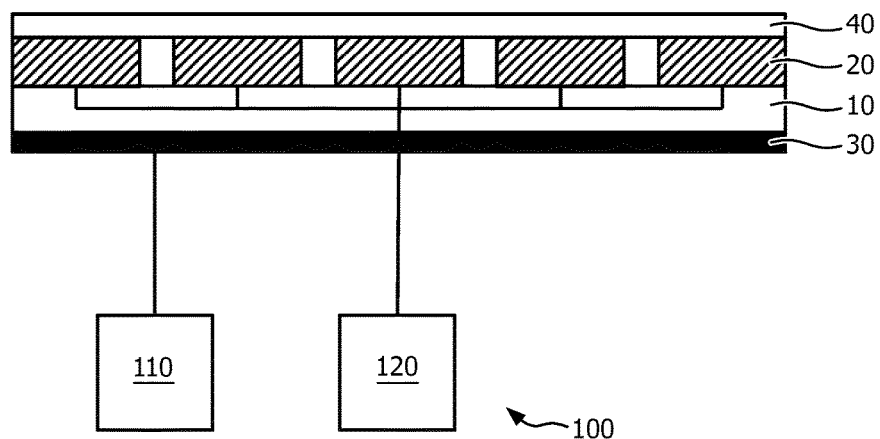
FIG. 10 schematically depicts an ultrasound system according to an embodiment.

FIG. 10 schematically depicts an ultrasound system 100 including an ultrasound array according to any of the aforementioned embodiments. The ultrasound system 100 typically comprises a driver arrangement 110 for providing the actuator arrangement 30 with appropriate drive signals, i.e. electromagnetic stimuli. The driver arrangement 110 is conductively coupled to the above described electrode arrangement(s) for deforming each of the one or more actuators of the actuator arrangement 30. The ultrasound system 100 further comprises an ultrasound signal generation stage 120 that is conductively connected to the aforementioned connections of the ultrasound transducer elements 20 for providing the ultrasound transducer elements 20 with control signals that trigger the generation of ultrasound signal transmissions by the ultrasound transducer elements 20. Such ultrasound signal generation stages 120 are well-known per se and may contain any suitable variety of components, such as a microbeam former, a main beam former, a transducer controller for controlling the direction in which beams are steered and focused, and so on. The driver arrangement 110 may be coupled to the signal generation stage 120 such that the beamforming signals for the individual ultrasound transducers 20 are synchronized with the driving signals for the actuator arrangement 30. In this embodiment an optimal beam steering conditions may be achieved combining the electrical steering of the transducers (enabled by the beamforming signals) and the mechanical steering of the actuator arrangement 30 (enabled by varying the arrays shape).

The ultrasound system 100 of FIG. 10 is an ultrasound therapy system such as a HIFU system and as such does not have to comprise an ultrasound echo processing stage. In such an embodiment, the ultrasound transducer elements 20 may be transmitter only elements. Such an ultrasound therapy system may be used for the treatment of any diseased tissue that can be reached using the focused ultrasound beam. A non-limiting example of such therapy is prostate therapy. As the ultrasound array may be realized using magnetic resonance-compatible materials only, the ultrasound system 100 of FIG. 10 may be used in magnetic resonance-guided therapy, where the ultrasound beam is focused and adjusted under guidance of a MRI system. MRI for instance may provide a real-time measurement of the temperature of the region of interest, thereby providing improved therapy control.

Figure 11:
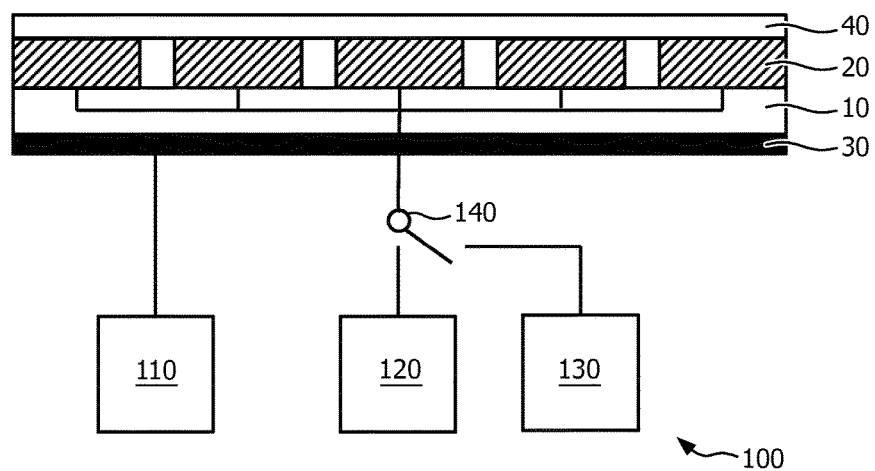
FIG. 11 schematically depicts an ultrasound system according to another embodiment.

FIG. 11 schematically depicts an alternative embodiment of the ultrasound system 100, in which the ultrasound system 100 further comprises an ultrasound echo processing stage 130. In this embodiment, the ultrasound system 100 is an ultrasound imaging system. The ultrasound signal generation stage 120 and the ultrasound echo processing stage 130 may be configurably coupled to the respective connections of the ultrasound transducer elements 20 through a transmitter/receiver switch 140 that switches the ultrasound system 100 between a transmit mode in which the ultrasound signal generation stage 120 is connected to the ultrasound array and a receive mode in which the ultrasound echo processing stage 130 is connected to the ultrasound array. Similarly, to the previous embodiment the driver arrangement 110 may be coupled to both the signal generation stage 120 and the ultrasound echo processing stage 130, such that the beamforming signals (for transmit and receive modes) for the individual ultrasound transducers 20 are adjusted in accordance the driving signals provided to the actuator arrangement 30.

Such ultrasound echo processing stages are well-known per se and may contain any suitable variety of components, such as a signal processor, which may be adapted to process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor optionally may perform additional signal enhancement such as speckle reduction, signal compounding, and noise elimination. The signal processor may implement a bandpass filter such as a tracking filter, with its passband sliding from a higher frequency band to a lower frequency band as echo signals are received from increasing depths, thereby rejecting the noise at higher frequencies from greater depths where these frequencies are devoid of anatomical information. Further elements may include one or more of a B-mode processor, a Doppler processor, a scan converter and a multiplanar reformatter, volume renderer and an image processor for further enhancement, buffering and temporary storage of the generated ultrasound image for display on an image display. As such components are routine components that are well-known per se, they will not be explained in further detail for the sake of brevity only.

In case of a deformed ultrasound array, beam forming of signals may be carried out for the ultrasound transducer cells 20 of the ultrasound array that have a clear acoustic view to the region of interest. Incoherent compounding may additionally be applied to these signals. Displacement vectors between actuated parts of the ultrasound array, i.e. displaced apertures, are required for correct beam forming and imaging. Such displacement vectors may be calculated on the fly using any available shape sensing technique for sensing the shape of the ultrasound array, such as optical shape sensing, position encoders that employ variable resistors, and so on.

The ultrasound systems of FIG. 10 or 11 may be utilized in minimum invasive healthcare interventions, in which both ultrasound and interventional X-ray may be used. The combination of ultrasound and X-ray increases the amount of information that can be obtained. Ultrasound and X-ray are two facilitating imaging modalities in minimally invasive interventions. For instance, X-ray fluoroscopy provides excellent instrument imaging and ultrasound shows high-quality images of soft tissue. Registration and optionally fusion of the acquired 2D or 3D images can improve the clinical workflow and procedural outcome.

Also, during a procedure it may be an option to use X-ray when starting the procedure and at certain other moments, e.g. when using fluoroscopy. By using ultrasound system 100 for the remainder of the procedure, the dose of X-ray radiation to which the patient is subjected is significantly reduced. Non-limiting examples of procedures in which such a hybrid approach can be beneficial include cardiac electrophysiology, ablation, atrial septal defect repair, left atrial appendage closure, mitral valve replacement, and so on. Other examples will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound array comprising:
a plurality of ultrasound transducer elements;
an actuator arrangement having an adjustable shape in response to an electromagnetic stimulus, wherein the actuator arrangement is deformed, at least partially, in correlation to the strength of the electromagnetic stimulus and the actuator arrangement comprises:
a first protective foil extending over the carrier;
a first plurality of strips extending over the first protective foil;
a second plurality of strips extending over the first protective foil, wherein the
second plurality of strips intersect the first plurality of strips; and
a second protective foil extending over the first and second strips; and and
a flexible carrier located between the ultrasound transducer elements and the actuator arrangement; and
wherein deformation of the actuator arrangement in response to the stimulus changes the orientation of one or more ultrasound transducer elements in response to said stimulus.

2. The ultrasound array of claim 1, wherein deformation of the actuator arrangement simultaneously changes the orientation of at least a subset of plurality of said ultrasound transducer elements.

3. The ultrasound array of claim 1, wherein the first plurality of strips perpendicularly intercept the second plurality of strips.

4. The ultrasound array of claim 1, wherein the first plurality of strips are interwoven with the second plurality of strip.

5. The ultrasound array of claim 1, wherein the ultrasound transducer elements are aligned with respective junctions of said first and second plurality of strips or with respective vacancies that are delimited by neighboring pairs of strips from the first plurality of strips and neighboring pairs of strips from the second plurality of strips.

6. The ultrasound array of claim 1, further comprising a protective foil, wherein the actuator arrangement is located in between the carrier and the protective foil.

7. The ultrasound array of claim 1, wherein the first plurality of strips, the second plurality of strips or both comprise an electro active polymer or an optically responsive polymer.

8. The ultrasound array of claim 1, further comprising a strap for securing the array against a body part.

9. An ultrasound system comprising:
the ultrasound array of claim 1;
an ultrasound signal generator coupled to the ultrasound transducer elements; and
an electromagnetic stimulus generator coupled to the actuator arrangement of the material having an adjustable shape.

10. The ultrasound system of claim 9, further comprising an ultrasound imaging stage coupled to the ultrasound transducer elements for generating an ultrasound image from ultrasound echoes received by the ultrasound transducer elements.

11. The ultrasound array of claim 1, wherein the ultrasound transducer elements are configured to transmit and receive signals for image generation.

12. The ultrasound array of claim 1, wherein the ultrasound transducer elements are configured to transmit focused signals for therapy.

* * * * *